(12) United States Patent
Ozero

(10) Patent No.: US 7,569,710 B1
(45) Date of Patent: Aug. 4, 2009

(54) ETHYLENE OXIDE RECOVERY PROCESS

(76) Inventor: Brian Ozero, P.O. Box 768, Westhampton Beach, NY (US) 11978

( * ) Notice: Subject to any disclaimer, the term of this patent is extended or adjusted under 35 U.S.C. 154(b) by 0 days.

(21) Appl. No.: 12/070,992

(22) Filed: Feb. 23, 2008

(51) Int. Cl.
*C07D 301/32* (2006.01)
*C07D 301/08* (2006.01)
*C07C 29/10* (2006.01)

(52) U.S. Cl. ............... 549/538; 549/523; 549/541; 568/867

(58) Field of Classification Search ............ 549/538, 549/523, 541; 568/867
See application file for complete search history.

(56) References Cited

U.S. PATENT DOCUMENTS

| | | | |
|---|---|---|---|
| 3,904,656 A | 9/1975 | Broz | |
| 3,964,980 A | 6/1976 | Ozero | |
| 4,134,797 A | 1/1979 | Ozero | |
| 4,822,926 A | 4/1989 | Dye | |
| 6,417,411 B2 | 7/2002 | Kakimoto et al. | |
| 6,846,966 B2 * | 1/2005 | Lumgair et al. | 585/639 |

* cited by examiner

*Primary Examiner*—Bernard Dentz
(74) *Attorney, Agent, or Firm*—Kenneth H Johnson

(57) ABSTRACT

An improved process for the recovery of a high-purity, ethylene oxide-water stream for use as feed to integrated ethylene glycol or ethylene oxide purification reactors by first contacting the gaseous effluent from ethylene oxide reactors with an aqueous alkaline quench solution water wash, then absorbing ethylene oxide from the washed vapor into process water to produce a dilute EO-water absorbate of which 10-90% is sent directly to the EO reabsorber/residual absorber, thereby bypassing the EO stripper.

1 Claim, 4 Drawing Sheets

ETHYLENE OXIDE RECOVERY PROCESS

BACKGROUND OF THE INVENTION

1. Field of the Invention

This invention relates to an improvement in the recovery of ethylene oxide (EO) from the gaseous effluent of ethylene oxide reactors, for use as feed to integrated glycol units for the production of polyester grade ethylene glycol (EG). More specifically, this invention relates to improved absorption/stripping systems for use in the EO recovery step of integrated EO/EG plants that will produce a purer ethylene oxide-water feed for the glycol plant, together with substantial savings in both energy consumption and capital investment.

2. Related Information

When ethylene oxide is produced by the silver-catalyzed, vapor-phase partial oxidation of ethylene by molecular oxygen, a hot gaseous reactor effluent is obtained. The ethylene oxide content is quite low, typically in the range of 1-3 mole % and recovery of the ethylene oxide from the effluent gas, as conventionally practiced, involves cooling of the gas in a heat exchanger train and absorption in water, producing a very dilute EO solution.

The function of the water absorption step is to selectively absorb the ethylene oxide from the reaction effluent gas with minimal concurrent absorption of other gaseous materials such as unconverted reactants, reaction diluents, and reaction by-products that are also present. However, since the absorber operates at relatively high pressure, usually only slightly below that of the reactor, and since substantial amounts of absorption water are required, significant amounts of by-product carbon dioxide and undesirable trace impurities such as formaldehyde, acetaldehyde and their acidic byproducts formed during the oxidation step may be concurrently absorbed, along with the ethylene oxide.

In the EO stripper, all of the absorbed ethylene oxide is stripped out using steam, along with all of the carbon dioxide and acetaldehyde, and substantial amounts of the formaldehyde, aldehydic acids, and impurities which may have been absorbed. The overhead vapor from the stripper is then cooled to condense out most of the water, a portion of the ethylene oxide, and most of the formaldehyde, acids and heavy impurities, which are returned to the stripper in some plants. The uncondensed stripper vapor contains the product ethylene oxide which is typically reabsorbed in recycle water from the glycol and EO purification units to produce a more concentrated aqueous solution which is pumped and used as feed to an EO purification system or converted to glycol in a glycol unit.

Even though the stripper typically operates at near-atmospheric pressure, the temperatures within the stripper are high enough to thermally hydrate a small, but a significant portion of the ethylene oxide to ethylene glycol. The glycol produced in the stripper is continuously removed as a dilute glycol-water purge, which is contaminated by formaldehyde, aldehydic acids and other impurities in some plants. The presence of aldehydes and aldehydic acids and impurities in any of the glycol unit feeds are highly undesirable since they result in byproducts in the glycol reactor, which lower the UV quality of the product glycols. It is difficult to upgrade the glycol content in the contaminated purge to polyester (fibre) grade quality, which is preferred, and the prior art includes patented process innovations for reducing the impurity levels in fibre grade glycol plant feeds.

U.S. Pat. No. 3,904,656, uses ion exchange and carbon bed treatment of the stripper bottoms bleed streams to remove acid salts and UV-absorbing impurities prior to adding it to the main glycol evaporation section.

U.S. Pat. No. 3,964,980, (commercially offered by Scientific Design Company Inc.) refluxes the condensed portion of the stripper overhead vapor that contains formaldehyde and aldehydic acids, back to the stripper to produce a higher purity reabsorber bottoms EO solution, which is the feed to the glycol reactor. The stripper bottoms bleed stream is treated as described in U.S. Pat. No. 3,904,656 before being added to the main glycol plant evaporation section.

In U.S. Pat. No. 4,822,926, (commercially offered by Shell Company) the EO reactor effluent from the heat exchanger is first sent to the quench section of an EO absorber. Here it is scrubbed with a recirculated, cooled aqueous alkaline stream to absorb and neutralize acidic compounds such as acetic and formic acids. Part of the trace amount of by-product formaldehyde is also absorbed. A quench bleed is then taken to remove the by-product water, which is partially condensed. The gases from the quench section pass into the main portion of the EO absorber where they are further scrubbed with cold water to recover the EO that is then purified or converted to fibre grade glycol. The quench bleed, which contains typically 0.5-3.0 wt. % of EO and comparable concentrations of glycol and sodium salts can be sent to a quench bleed stripper where EO is stripped out and recovered. The EO-free quench stripper bottoms can then be disposed of as a waste stream or processed separately for technical grade glycol recovery. Alternatively, the quench bleed containing EO can be passed through a pipe reactor to convert the EO to glycol and then processed to recover technical grade glycol and discard the salts, formaldehyde and water.

U.S. Pat. No. 6,417,411 teaches an EO/EG process which incorporates an EO absorber/stripper flow scheme similar to that described in U.S. Pat. No. 3,964,980, in which the stripper bottoms bleed stream is fed to the "by-produced glycol concentration column" where much of the water in the feed is stripped out, producing a concentrated by-product glycol stream that is then processed separately from the main glycol product to recover the glycol content.

The process described in U.S. Pat. Nos. 3,904,656, 3,964,980 and 6,417,411, effectively prevent salts, acids and most of the heavy aldehydic impurities from contaminating the polyester glycol product of integrated EO/EG plants reaction flowschemes, but do not adequately reduce the formaldehyde contamination of the combined glycol plant feed streams. As a result, the formaldehyde concentration in the recycled glycol reaction water builds up and produces undesirably high amounts of heavy aldehydic impurities by reacting with ethylene oxide or ethylene glycol in the main glycol reactor. Many of these heavy aldehydic impurities end up in the ethylene glycol distillate and negatively affect the UV quality of the fibre grade glycol product.

The art therefore has long needed a simple, low-cost and efficient system for EO absorption flowschemes that adequately reduces the formaldehyde content of the feed streams to polyester grade glycol units, eliminates the costly treating of bleed stream feeds and/or product polyester grade glycol, and obviates the need for co-producing technical grade ethylene glycol. To limit the production of less desirable diethylene glycol, all non-catalytic, adiabatic glycol reactors, which are the most usual, operate with very high water/EO molar ratios, FIG. 1, prepared from research data published in the literature, shows that at a 22:1 water/EO molar ratio (10 wt. % EO), the theoretical MEG yield would be about 91.5 mol. %, equivalent to about 92.7 wt % MEG in the product glycols. However, the literature reports that at high water/EO ratios in commercial reactors, the selectivities to monoethylene glycol (MEG) and the MEG yields are "somewhat lower" than those predicted from FIG. 1.

As can be seen from FIG. 1, the beneficial effects on MEG yields of increasing the water recycle start to decrease rapidly above water/EO ratios of 15. Accordingly, in optimizing the design of the glycol plant, the improved MEG yields resulting from increasing the water recycle are balanced against increased capital and utility costs. As a result, commercial non-catalytic plants usually operate with water/EO ratios in the range 18-25:1 (equivalent to EO concentrations of 12-8.5 wt %). Thus, the art has also needed a low-cost and energy efficient way of being able to increase the water/EO molar ratios in the glycol reactor to 30-35:1 to increase the yield of the desired product, monoethylene glycol.

An advantage of this invention is increased production of polyester grade ethylene glycol by reducing the amount of glycol bleeds or off-specification products that are degraded to lower value technical grade products produced when using the prior art EO recovery procedures.

SUMMARY OF THE INVENTION

Briefly the present invention is an improvement in the process or recovering ethylene oxide from a vaporous reaction stream containing ethylene oxide, $CO_2$, formaldehyde, acetylaldehyde, and organic acidic compounds comprising:

absorption of ethylene oxide and a portion of said $CO_2$, formaldehyde, acetylaldehyde, and organic acidic compounds in water to form a absorption stream;

contacting said absorption stream with steam to strip ethylene oxide, $CO_2$, formaldehyde, acetylaldehyde, and organic acidic compounds from said absorption stream to form a stripping stream condensing water, formaldehyde, a portion of the ethylene oxide, acetaldehyde and organic acidic compounds; and recovering a vaporous ethylene oxide product stream:

wherein the improvement comprises first feeding said vaporous reaction stream to a lower section of a quench zone, contacting the vaporous reaction stream with a dilute aqueous solution of alkaline hydroxide solution in said lower section, wherein said alkaline hydroxide reacts with $CO_2$, to form carbonate and bicarbonate compounds, which react with and neutralize organic acid impurities, contacting the vaporous reaction stream from the lower section and a liquid water stream with a first demister mesh, contacting a vaporous reaction stream from said first demister mesh with a second demister mesh in an upper section of said quench zone, and recovering a pretreated vaporous reaction stream.

In a preferred embodiment the pretreated vaporous reaction stream is fed to a water wash section in which it is washed with fresh process water to absorb any remaining entrained quench liquid and formaldehyde vapor, passing said pretreated vaporous reaction stream from the water-wash section through a liquid de-entrainment device and feeding it to the bottom of the EO absorber where it is countercurrently washed with recirculated, EO-free process water to absorb the ethylene oxide to produce EO containing absorbate sending a first portion comprising 10-90% and preferably 15-75% of the dilute, EO containing absorbate from the EO absorber directly to a EO reabsorber/residual absorber where it absorbs additional EO from an EO stripper overhead vapor to produce high-purity EO/water solution of the desired EO concentration for use as feed to a glycol reaction or EO purification, sending a second portion comprising the balance (90-10% and preferably 85-25%) of the dilute, EO containing absorbate from the EO absorber to the EO stripper where the EO and absorbed, non-condensible gases are completely stripped out by steam, and a EO free bottoms stream is cooled and recycled back to the EO absorber, In accordance with this invention, in plants using an EO recovery flowscheme similar to that described in U.S. Pat. No. 3,964,980 (which relates to plants designed by Scientific Design), the absorber system will be replaced by an efficient quench-absorber but the basic EO stripper-reabsorber system will be retained. The separate quench column (or the bottom section of a new absorber) is designed to thoroughly scrub the EO reactor effluent gas with recirculated, cooled, dilute alkaline solution, of 1 to 30%, preferably 1 to 15% solution of alkaline hydroxide. to neutralize the organic acids and absorb the maximum amount (ca. 90-98%) of the formaldehyde, and other heavy (in water) aldehydic impurities. The scrubbed gas from the quench section will be passed through a high-efficiency, demister mesh to remove entrained quench solution and will then be washed with a small amount of once-through (and/or recirculated) fresh water to remove any entrained quench liquid and absorb more formaldehyde. The effluent wash water from the wash section then drains into the lower quench section to reduce the concentration of formaldehyde and absorbed impurities and permit their more complete removal in the quench solution.

The washed cycle gas, which will be almost completely free of formaldehyde and heavy impurities and completely free of acids, will be passed though a demister mesh to remove entrained wash liquid and then thoroughly scrubbed in the absorber with once-through process water (recycled from the stripper and glycol unit) to completely absorb ethylene oxide and produce a dilute (1-5 wt. %) EO-water solution.

DETAILED DESCRIPTION OF THE INVENTION

Figure 1:
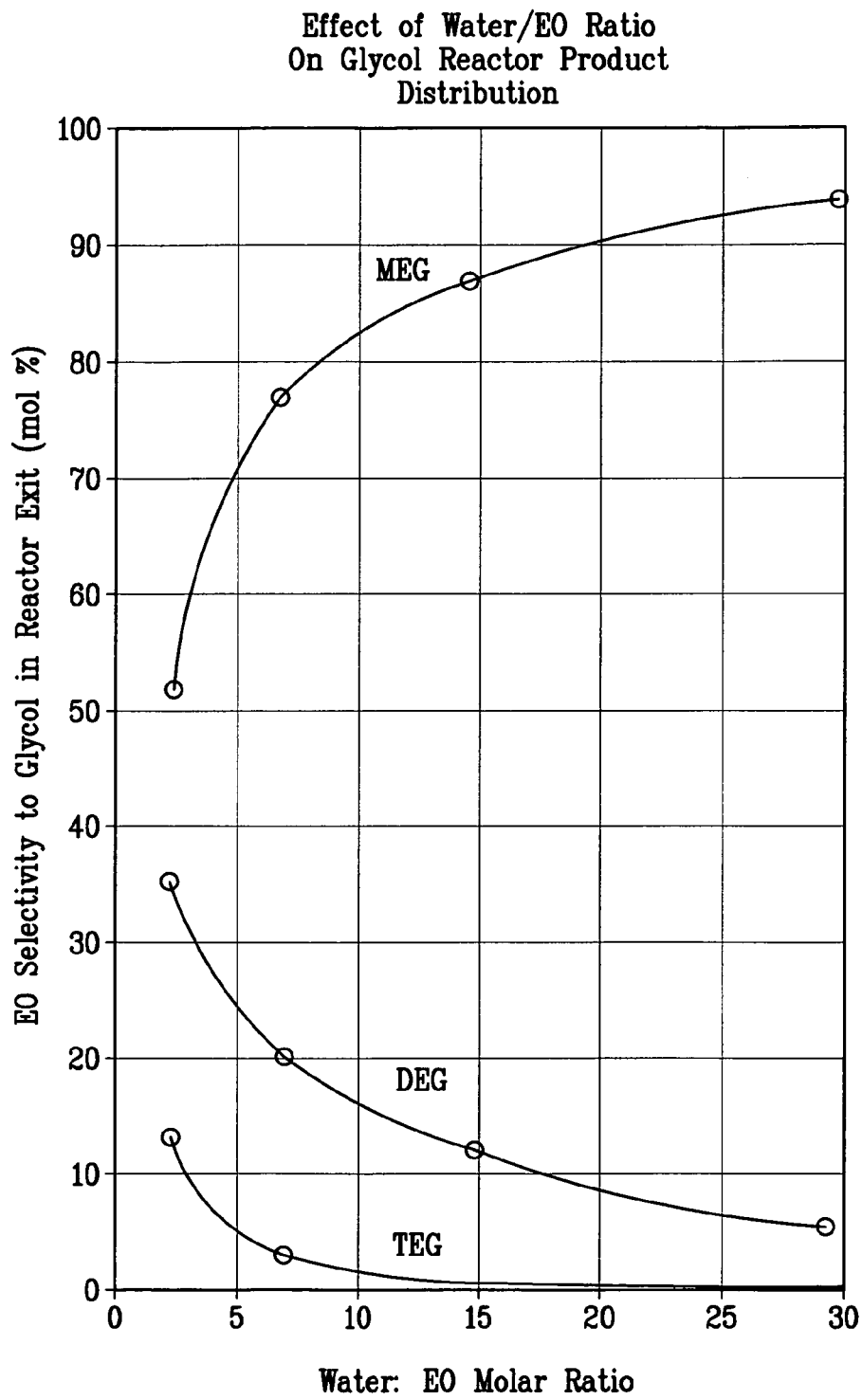
FIG. 1 is a graph showing the effect of Water/EO ratio on glycol reactor product distribution.

Most of the water formed in the EO reactor is condensed in the quench scrubber. To maintain the water balance in the quench water system, a net purge of the alkaline quench condensate plus wash water is required. Since the total quench bottoms purge will also contain a small concentration (1-4 wt. %) of EO, it will be stripped of its EO content in a small purge stripping column which will operate in parallel with the main stripper. To avoid contaminating the main stripper product EO vapor with formaldehyde and entrained acid salts from the small purge stripper, the overhead EO-rich vapor from the purge stripper will be partially condensed and the contaminated condensate will be returned as reflux to the purge stripper. The EO-free bottoms from the quench purge stripper will thus contain almost all of the formaldehyde and heavy aldehydic impurities and all the (neutralized) acids produced in the EO reaction system. Since the amount of glycol in this small purge (produced by hydration of EO in the quench scrubber and purge stripper) is extremely small, it usually does not justify the installation of dedicated purge glycol recovery facilities, and it can be sent directly to waste treatment in most plants. Alternately, the quench/wash purge could be processed for recovery of the glycol content as technical grade product.

The dilute EO-water bottoms stream from the absorber, which is free of organic acids, and essentially free of formaldehyde and heavy contaminants, will be completely stripped of EO and dissolved gases in the main EO stripper. The overhead EO and water-rich vapor is cooled and partially condensed in an overhead heat exchanger, which can be cooled using air or cooling water. Unlike the process described in U.S. Pat. No. 3,964,980, both the vapor and condensate effluent from the main stripper condenser is fed to the reabsorber, since the condensate which is rich in EO is also essentially free of impurities. This improves the efficiency of the EO stripping/reabsorption step compared to that of the prior art.

In the improved process, high-purity EO-water bottoms from the EO absorber would produce fibre grade glycol if used as feed to an integrated glycol plant after removal of $CO_2$ and other absorbed non-condensible gases. Unfortunately, based on industry information, the concentration of ethylene oxide in the dilute EO absorbate is too low in commercial EO reaction systems to permit its economical use as direct feed to a glycol reactor and evaporation system. By incorporating the improvements described herein, a substantial portion of the EO absorbate does not need to be stripped of its EO in the main EO stripper, and can be sent directly to the EO stripper overhead condensing/reabsorption system to absorb more ethylene oxide so that it can then be used as direct feed to the glycol reactor. This reduces the operating and capital cost of the EO absorption system and makes the use of water/EO molar ratios that are higher than 25:1 more economical.

Figure 4:
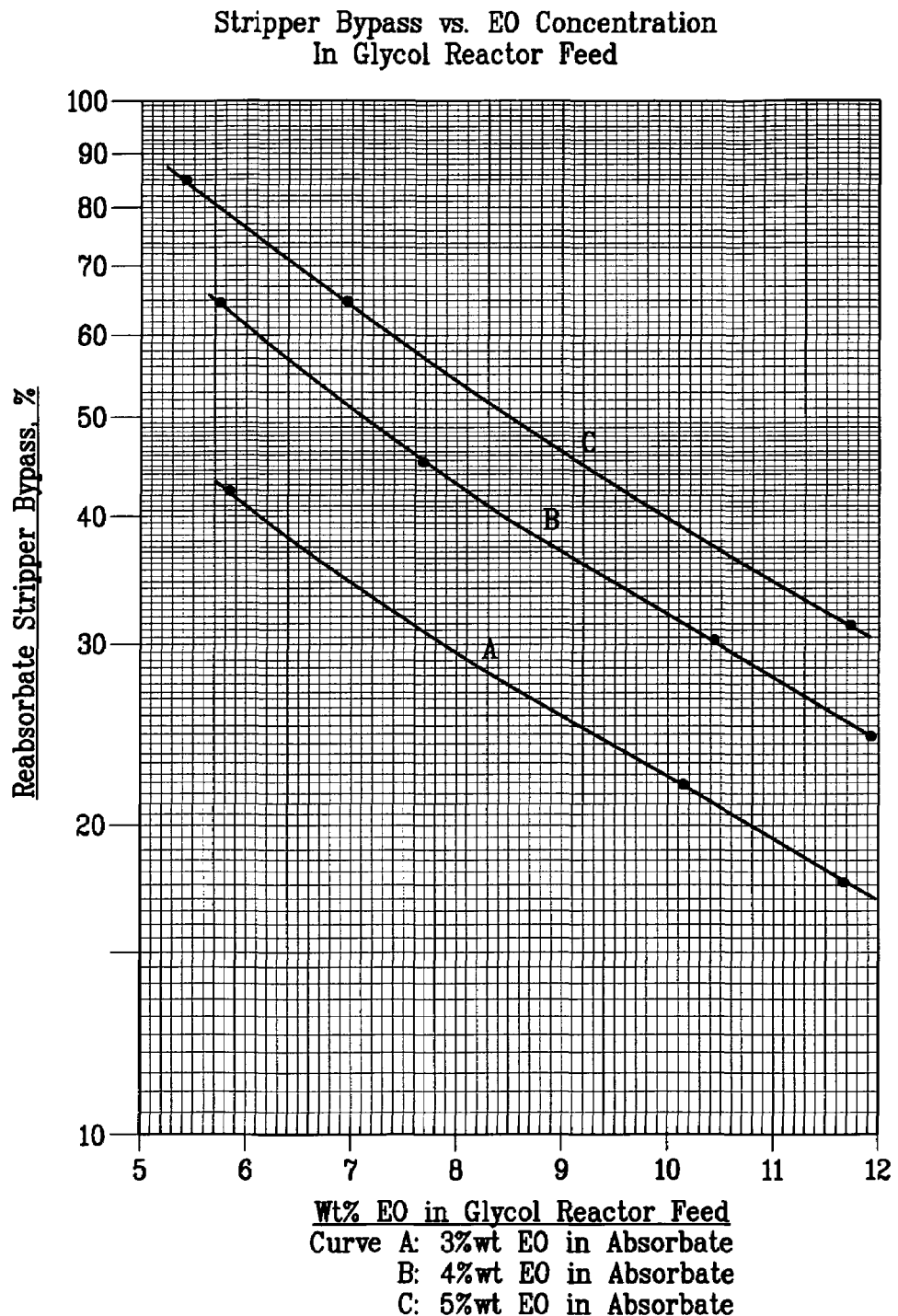
FIG. 4 shows the maximum potential stripper bypass rates (and the related stripper savings) increase as the concentration of EO in the absorbate increases, and as the water-to-EO ratio in the glycol reactor feed is raised to reduce the production of heavier glycols.

Accordingly, in a commercially significant feature of this invention (reference FIG. 4), up to 90% but preferably 15-75% of the impurity-free, EO absorber bottoms can be fed directly into the reabsorption system, bypassing the EO stripper. As shown in FIG. 4, the maximum potential stripper bypass rates (and the related stripper savings) increase as the concentration of EO in the absorbate increases, and as the water-to-EO ratio in the glycol reactor feed is raised to reduce the production of heavier glycols. The flowrate of reabsorption feed water, which is recycled water from the glycol plant evaporation (and EO purification section), is reduced proportionately to produce the desired concentration of EO (typically 6-12 wt. %) in the reabsorber (or light ends column) bottoms.

The water balance in the absorber-stripper system may be maintained by injecting low pressure process steam extracted from the glycol plant directly into the EO stripper to provide up to 100% of the stripping vapor required (which is an additional benefit of this invention) or by recycling water from the glycol plant evaporation section for use as absorption water.

A further major saving for improved SD-type EO flowschemes resulting from the application of this invention, is the elimination of the costly stripper bottoms (cycle water) bleed treating systems such as described in U.S. Pat. No. 3,904,656 or separate byproduct glycol concentration and recovery facilities described in U.S. Pat. No. 6,417,411.

The improved stripper bypass flowscheme permits very high "bleed" rates of EO cycle water to the glycol plant without costly pretreatment. As a result the equilibrium glycol concentration in the EO absorber-stripper cycle can be reduced to very low concentrations (<1 wt. %) compared to the much higher concentrations (3-6 wt. %) that are typical for standard stripper systems. The lower MEG concentration reduces the foaming tendency of the water absorbent in both the EO absorber and the EO stripper and thus increases the capacity and efficiency of the trays or packing in those columns. Thus the application of this invention to EO absorber-stripper systems in new plants will save both initial investment capital and continuous energy usage.

The stripper bypass concept can also have great benefits for existing EO plants that wish to expand the capacity of their existing EO reaction and recovery sections. The application of this invention will debottleneck the EO absorber-stripper system very simply, at minimum capital cost, and also provide significant reduction in energy consumption (and $CO_2$ production), which has now become a major environmental as well as economic consideration.

The removal of essentially all the formaldehyde produced in the EO Reactor from the feed steams to the glycol unit will result in the production of fewer UV-absorbing impurities in the glycol reactor and improve the fiber-grade glycol quality. Accordingly, another major potential benefit of the application of this invention to SD-type EO reaction/recovery systems similar to that described in U.S. Pat. No. 3,964,980, is that it would permit the use of ultra-high selectivity EO catalysts, which (as is known in the industry) may generate high amounts of formaldehyde that would normally adversely affect the UV quality of glycol produced in standard SD-type integrated glycol units that produce only fibre grade MEG.

The Shell type EO process, as described in U.S. Pat. No. 4,822,926, includes a quench scrubber and quench stripper, which are essential steps of the improved EO recovery process. However, these two process steps, as described in the patent, cannot produce EO absorber bottoms that are completely contaminant-free and suitable as direct feed to a fibre grade glycol reactor, and in the patent flowscheme, 100% of the EO absorbate is fed to the EO stripper. By incorporating this invention and increasing the absorption efficiency of the quench section by adding a water wash and reducing inter-stage and inter-section entrainment in the quench-wash column, the rich EO absorbate will be pure enough for use as direct feed to the glycol plant. As a result, a significant portion (15-75%) of the EO absorbate can then bypass the EO stripper and be injected directly into the stripper overhead EO recovery section.

In addition, to avoid any contamination from the quench bleed solution in the present improved flowscheme, the EO-rich overhead vapor from the quench stripper (e.g., in the Shell process) will be partially condensed and the condensate, contaminated with entrained salts and condensed formaldehyde, will be returned as reflux to the quench stripper. The net ethylene oxide vapor and uncondensed steam will flow directly to the residual EO absorber for recovery of the EO vapor as glycol reactor feed. The EO-free bottoms from the improved quench bleed stripper will then contain essentially all of the formaldehyde and heavy aldehydic impurities and all the (neutralized) acids produced in the EO reaction system. Since the amount of glycol in this small purge (produced by hydration of EO in the quench scrubber and stripper) is extremely small, it can be sent directly to waste treatment with minimum economic loss if existing purge glycol recovery facilities are not available.

The current UV transmittance sales specifications, which are as follows:

|  | UV Transmittance, % |
| --- | --- |
| At 220 nm | 80 min |
| At 275 nm | 95 min |
| At 350 nm | 99 min |

The major contributor to the production of impurities in the glycol hydration reactor, which adversely affect the UV transmittance of the fibre grade ethylene glycol product is the formaldehyde that is introduced via the treated cycle water bleed and that builds up in the glycol reaction recirculated water.

Figure 2:
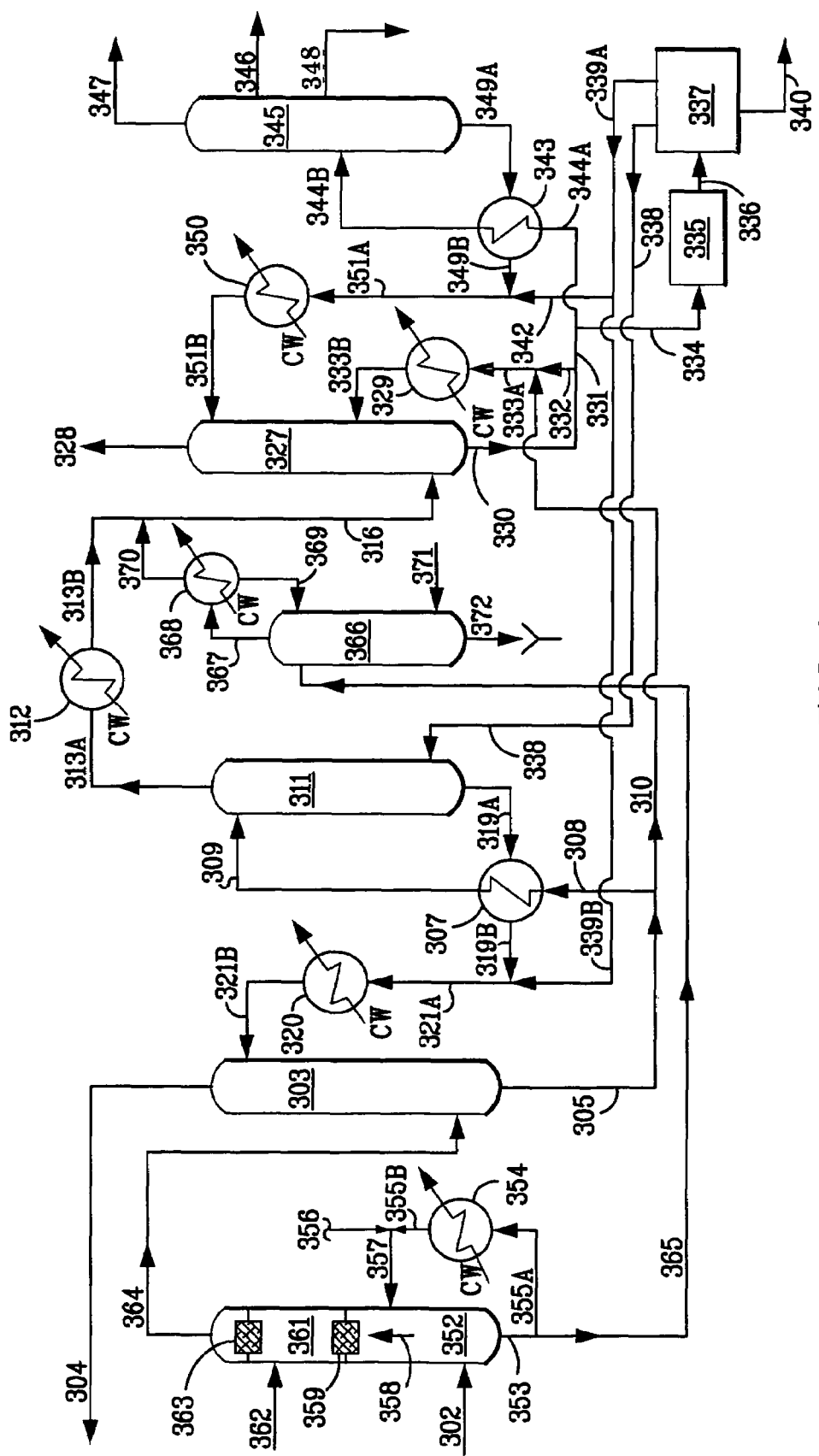
FIG. 2 is a schematic representation of the incorporation of the improved process into the flowscheme of a prior art recovery system such as that described in U.S. Pat. No. 3,964,980, which consists of the new wash/quench column and the quench purge stripper, and the addition of a rich EO absorbate bypass directly to the EO reabsorber.

The embodiment of this invention as applied to plants described in U.S. Pat. No. 3,964,980, is shown in FIG. 2. Referring to FIG. 2, effluent gas from the EO Reaction system containing ethylene oxide is introduced directly into the bottom section of quench column 352 via conduit 302. Quench bottoms solution is recirculated via conduits 353 and 355A, cooler 354, and conduits 355B and 357 to the top of the quench scrubbing section. Concentrated sodium hydroxide (10-20 wt. % aqueous solution) is injected into the recirculated quench solution via conduit 356 to be converted into sodium carbonate and bicarbonate and neutralize organic acids. The cooled, scrubbed vapor from the top of the quench section 352, which is free of organic acid vapor but contains some formaldehyde and entrained quench liquid is passed through a demister mesh 359 to remove the entrained liquid and enters the upper wash section 361.

The filtered quench gas leaving the quench demister 359 is then washed with fresh process water, introduced via conduit 362 to completely remove any remaining entrained quench liquid and absorb most of the remaining formaldehyde and heavy impurities. A countercurrent water wash will preferably be used, which can be preceded by a recirculated water wash section for maximum vapor-liquid contact. The net wash water from the bottom of the water wash section(s) will drain into the top of the lower quench section 352, diluting the concentration of formaldehyde and other undesirable impurities in the quench liquid and reducing the equilibrium concentration of these impurities in the scrubbed gas feed to the EO absorber. The net quench bottoms solution bleed, containing condensed water, wash water, absorbed impurities and some ethylene oxide, flows via conduits 353 and 365 to quench bleed stripper 366.

The washed vapor from the top of the water wash section, is passed through demister mesh 363 to remove any entrained wash water and enters the bottom of the EO absorber 303 via conduit 364. Cold absorption water is introduced into the upper section of absorber column 303 via conduit 321B and the reaction effluent gas is countercurrently contacted by the water to absorb almost all of the ethylene oxide entering via conduit 364. The non-condensible reaction gas leaving the top of absorber 303 is essentially free of ethylene oxide and is returned to the EO reaction system via conduit 304. The dilute EO-water solution that is formed in absorber 303 is withdrawn from the bottom of the absorption section via conduit 305.

In FIG. 2 the quench/wash column is shown as a separate vessel for clarity of depiction. However in actual plants, the EO absorber, water wash, and alkaline quench sections can be combined into one shell to minimize pressure drop and capital cost.

In this flowscheme, part of the EO absorbate in conduit 305 bypasses EO stripper 311 and flows directly to the EO reabsorber bottoms recycle cooler 329 via conduits 310 and 333A. The amount bypassed will vary between 15-75% depending on the EO concentration in the absorbate and the desired EO concentration in the reabsorber bottoms (and glycol reactor feed), and can be determined using tables, equations, or graphs such as shown in FIG. 4.

The balance of the absorbate is introduced into the stripper preheater exchanger 307 via conduit 308, and the hot rich absorbate from preheater 307 is fed to an upper portion of EO stripper 311, via conduit 309. Stripping steam extracted from the glycol plant is introduced to a lower portion of stripper 311 via conduit 338 or generated internally by a reboiler (not shown). By countercurrent contact of the absorbate and steam within stripper 311, the absorbate is stripped of the ethylene oxide, which together with steam, carbon dioxide, light ends and trace impurities is withdrawn from the top of stripper 311 via conduit 313A. The stripped (lean) absorbate, now essentially free of ethylene oxide, is withdrawn from the bottom of stripper 311 via conduit 319A and cooled in heat exchanger 307, giving up heat to the rich absorbate feed. The cooled lean absorbate from cooler 307 is passed via conduit 319B, combined with recycled water from the glycol plant in conduit 321A to heat exchanger 320, where it is further cooled and the total lean absorbate stream is recycled back to absorber 303 via conduit 321B.

The rich absorbate feed to stripper 311 may contain from about 1 to about 5 wt. % of ethylene oxide and the stripper is operated to recover more than 95% and usually more than 99% of the ethylene oxide contained in the stripper feed. Though the stripper normally operates at close to atmospheric pressure, the temperatures in the column are high enough to thermally hydrate in the range of 0.5-3.0% of the EO feed to ethylene glycol. The glycol produced in the EO stripper will build up to a low, equilibrium concentration that is controlled by the absorbate bypass (via stream 310), which acts as a very large cycle water glycol bleed.

The stripper overhead vapor withdrawn via conduit 313A, usually contains about 20 to 30 mole % of ethylene oxide. The primary diluent in this vapor stream is water, although about 7-10% can be generally referred to as non-condensible gases, predominantly $CO_2$, but also including nitrogen, argon, oxygen, methane, ethylene and ethane. The stripper overhead vapors are cooled in heat exchanger 312 and the total effluent mixture of uncondensed vapor and condensate flows via conduits 313B and 316 to the reabsorber 327.

The net bleed bottoms stream from quench column 352 consists mainly of the EO reaction byproduct water that is partially condensed in the quench scrubber plus makeup wash water, and contains some alkaline salt and absorbed ethylene oxide. This stream is sent, via conduit 365, to a small purge stripper 366 where the contained ethylene oxide is stripped out, using stripping steam injected via conduit 371, or generated in a reboiler (not shown). A purge stripper feed/bottoms heat exchanger may be also used to reduce the reboiler heat duty and/or the amount of stripping steam. The purge stripper overhead vapors are cooled in heat exchanger 368 to a temperature such that a substantial part, preferably at least 60%, of the contained water is condensed. The contaminated condensate phase from condenser 368 is drained or pumped back into the upper portion of the purge stripper 366 via conduit 369. The uncondensed purge stripper overhead vapor is withdrawn from condenser 368 via conduit 370, combined with the EO and condensate mixture from main stripper condenser 312 in conduit 316 and introduced into a lower portion of the reabsorber 327. The EO-free aqueous bottoms from purge stripper 366, containing most of the formaldehyde, salts, and a small amount of ethylene glycol are sent to waste treatment or technical grade glycol recovery via conduit 372.

Some recycle cold water is introduced to an upper portion of reabsorber 327 via conduit 351B. Within the upper portion of the reabsorber, the light gases in the stripper overhead vapor and the water are countercurrently contacted to absorb the maximum amount possible of the ethylene oxide contained in the vapor. The non-condensed gases from the top of reabsorber 327, normally containing only trace amounts of ethylene oxide are vented via conduit 328. Since this vent stream contains a significant amount of hydrocarbons, consisting mainly of ethylene and methane, it is preferably compressed and recycled back to the ethylene reactor gas system for (partial) recovery of the contained ethylene. In some plants, particularly those of small production capacity, the reabsorber vent gas is vented to atmosphere, or preferably incinerated to avoid atmospheric pollution.

The EO-rich reabsorbate is withdrawn from the bottom of reabsorber 327 via conduit 330. The reabsorbate is pressurized using a pump (not depicted) and divided into two portions. The portion which is the net bottoms product flows through conduits 331 and 334 to the glycol reaction system 335 and/or may flow via conduit 344A to EO purification unit 345. The aqueous reabsorbate bottoms contain not only the reabsorbed ethylene oxide vapor but also contain acetaldehyde and dissolved carbon dioxide and other organic and inorganic gases. As described in U.S. Pat. No. 4,134,797, the EO-rich reabsorbate withdrawn via conduits 330 and 331 will first pass into a carbon dioxide stripping column (not shown), wherein the liquid is stripped of $CO_2$ and other dissolved gases which are recycled back to the bottom of reabsorber 327 for recovery of contained ethylene oxide vapor. The gas-free bottoms from the carbon dioxide stripping column are then pumped to the glycol reaction and EO purification units, as described in U.S. Pat. No. 3,964,980.

The recycled reabsorbate flowing through conduit 332 is combined with bypassed rich absorbate in conduit 333A, cooled in heat exchanger 329 and introduced as cold liquid to a middle portion of reabsorber 327 via conduit 333B. Heat exchanger 329 maintains the reabsorber in heat balance to achieve the pre-determined bottom reabsorbate temperature and concentration of ethylene oxide. Depending on the operating pressure of the reabsorber and the amount of bypassed dilute absorbate, the ratio of reabsorbate recycled via conduit 332 to the net reabsorbate withdrawn via conduit 331 will range from 0-3:1. The maximum bypass of rich absorbate (not shown) may be achieved when the bypassed absorbate in stream 310 is separately cooled and introduced into reabsorber 327 at a point above the recycled bottom reabsorbate.

The reabsorbate flowing to EO purification is preheated in heat exchanger 343 and fed to the lower part of a single EO purification column 345 where it is separated into purified EO product (stream 346), and two formaldehyde and acetaldehyde-rich crude EO purge streams (streams 347 and 348, respectively) which are fed to the glycol reactor 335. The EO-free bottom water stream containing most of the trace amount of formaldehyde in the purification feed, is withdrawn via conduit 349A, cooled in heat exchanger 343 and recycled to the reabsorber 327 via conduit 349B.

In the glycol reactor 335, the ethylene oxide in the degasified reabsorber bottoms is almost completely reacted with water to form ethylene glycols. The effluent from the glycol reactor 335, is fed to a multiple-effect evaporation train 337 in which the water is separated from the crude glycol that is then fed to glycol purification (not shown) via conduit 340. Part of the water separated in evaporation train 337 is recycled back to the EO plant as steam via conduit 338 and injected directly into EO stripper 311 to provide up to 100% of the required stripping steam. The balance of the recovered water is condensate that is recycled back to the EO plant via conduits 339A and 342, combined with EO refiner 345 bottoms in conduit 351A, cooled in cooling unit 350 and fed to the to of reabsorber 327 as the reabsorbate via conduit 351B. To maintain the water balance in the EO stripper 303, makeup glycol recycle water can be added via conduits 339B, 321A and 321B.

The improved flow scheme depicted in FIG. 2 and described herein will produce fibre grade MEG that will significantly exceed the current UV transmittance sales specifications, which were shown previously.

Figure 3:
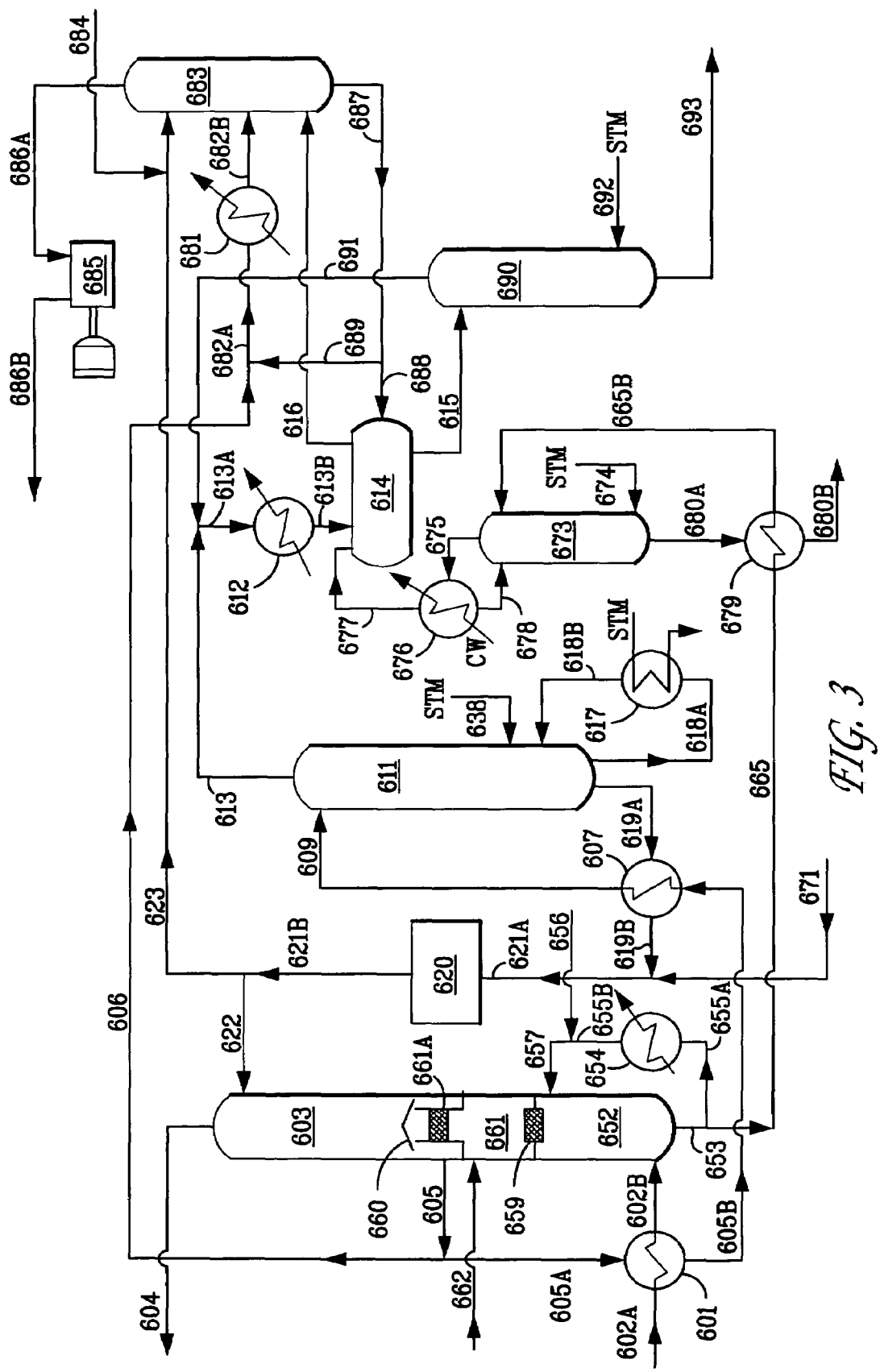
FIG. 3 is a schematic representation of the incorporation of the improved process into the flowscheme of a prior art recovery system such as that described in U.S. Pat. No. 4,822,926, which consists of the improved wash/quench column and modified EO stripping system, with the injection of the rich EO absorbate stripper bypass into the residual absorber to absorb more EO.

The embodiment of this invention as applied to integrated EO/EG plants with an EO recovery flowscheme comparable to that U.S. Pat. No. 4,822,926, is shown in FIG. 3. Referring to FIG. 3, effluent gas from the EO Reaction system containing ethylene oxide is passed via conduit 602A, gas cooler 601, and conduit 602B into EO quench section 652 of the EO absorption column, as before. Quench bottoms solution is recirculated via conduits 653 and 655A, cooler 654, and conduits 655B and 657 to the top of the quench scrubbing section 652. Sodium hydroxide is injected via conduit 656 into the recirculated quench solution to be converted into sodium carbonate and bicarbonate and neutralize organic acids. In a new plant, the gas cooler 601 shown in FIG. 6 can be omitted by increasing the quench recirculation rate and the heat duty of the quench cooler, and by the addition of 1-4 more quench trays.

The cooled, scrubbed vapor from the top of quench section 652, which is free of organic acid vapor but contains some formaldehyde and entrained quench liquid is passed through a demister mesh pad 659 to remove the entrained liquid and enters the upper wash section 661 via an internal vapor conduit (not shown). The filtered quench gas leaving quench demister 659 is then washed with fresh process water (stream 662) to completely remove any remaining entrained quench liquid and absorb most of the remaining formaldehyde and heavy impurities. A countercurrent water wash will preferably be used, which can be preceded by a recirculated water wash section for maximum vapor-liquid contact. The net wash water from the bottom of the water wash section(s) 661 will drain into the top of the lower quench section 652, diluting the concentration of formaldehyde and other undesirable impurities in the quench liquid and reducing the equilibrium concentration of these impurities in the scrubbed gas feed to the wash section. The net quench bottoms solution bleed, containing condensed water, wash water, alkaline salts, absorbed impurities and some ethylene oxide, flows via conduits 653 and 665 to quench bleed stripper 673.

The washed vapor from the top of the water wash section, is passed through demister mesh 661A to remove any entrained wash water and enters the bottom of EO absorber 603 via internal conduit 660. In EO absorber 603, the EO contained in the quenched reaction gas is absorbed by countercurrent contact with cold, recycled absorption water introduced via conduit 622. The non-condensible reaction gas leaving the top of absorber 603 is essentially free of ethylene oxide and is returned to the EO reaction system via conduit 604. The EO-rich absorption bottoms exit via conduit 605, and a portion (15-75%) bypasses the EO stripper and is sent directly, via conduits 606, 682A and 682B and new reabsorption cooler 681, to the middle section of the residual absorber 683 where it absorbs more ethylene oxide.

The balance of the rich absorbate flows via existing conduit 605A to gas cooler 601 and enters stripper preheater exchanger 607 via conduit 605B. The hot rich absorbate from preheater 607 is introduced into the upper part of EO stripper 611, via conduit 609. In EO stripper 611, the dissolved ethylene oxide and other light components are stripped out using stripping steam generated in reboiler 617 and/or injected directly as live steam (stream 638). The stripped (lean) absorbate, now essentially free of ethylene oxide, is withdrawn from the bottom of stripper 611 via conduit 619A and cooled in heat exchanger 607, giving up heat to the rich absorbate feed. The cooled lean absorbate from cooler 607 is passed via conduit 619B, combined with recycled water from glycol evaporation and EO purification (stream 671) in conduit 621A to cooling unit 620, where it is further cooled and recycled back to absorber 603 via conduits 621B and 622. A portion of the cold lean absorbate from cooler 620 can be sent via conduit 623 to the top of residual absorber 683 to absorb ethylene oxide from the light gas vent. Alternatively, cold recycled water from the glycol and EO purification units (stream 684) could be injected directly into reabsorber to replace all or part of stream 623.

The stripper overhead vapor withdrawn via conduit 613 can be expected to contain about 20 to 30 mole % of ethylene oxide. The primary diluent in this vapor stream is usually water, although about 7-15% are non-condensible gases, predominantly $CO_2$, but also includes nitrogen, argon, oxygen, methane, ethylene and ethane. The stripper overhead vapors are combined with the overhead vapor from the light ends column 690 in conduit 613A and are cooled and partially condensed in heat exchanger 612. The total effluent mixture of uncondensed vapor and condensate from condenser 612 flows via conduit 613B into separator 614 where the vapor and liquid are separated.

The EO-rich vapor flows from separator 614 via conduit 616 to the bottom portion of residual absorber 683. Within the top portion of residual reabsorber 683, the light gases in the stripper overhead vapor are countercurrently contacted by cold recycle water to absorb the maximum amount possible of the ethylene oxide contained in the vapor. The non-condensed gases from the top of reabsorber 683, normally containing only trace amounts of ethylene oxide are vented via conduit 686A. Since this vent stream contains a significant amount of hydrocarbons, consisting mainly of ethylene and methane, it is preferably compressed in compressor 685 and recycled back to the ethylene reactor gas system for (partial) recovery of the contained ethylene. In some plants, particularly those of small production capacity, the residual absorber vent gas may be vented to atmosphere or, preferably, incinerated to avoid atmospheric pollution.

The EO-rich reabsorbate is withdrawn from the bottom of residual absorber 683 via conduit 687. The reabsorbate is pressurized using a pump (not depicted) and divided into two portions. The portion which is recycled flows through conduit 689 and after combining with the bypassed rich absorbate in conduit 682A, is cooled in heat exchanger 681 and enters the mid-section of residual reabsorber 683. The net reabsorbate product flows via conduit 688 to separator 614 where it is combined with the condensate from condenser 612 and enters the upper part of the light ends column 690 via conduit 615. In light ends column 690 the reabsorbate solution is stripped of $CO_2$ and other dissolved gases which are recycled back via conduit 691 to stripper condenser 612 and residual absorber 683 for recovery of contained ethylene oxide vapor. The lights-free bottoms from light ends tower 690 are then pumped to the glycol reaction and EO purification units (not shown) via conduit 693.

The improved EO quench/wash system of the present invention reduces formaldehyde and other contaminants in EO absorbate making it suitable as direct feed to glycol reaction, and improving MEG quality. Also the improved EO quench cooling system design afforded by the improved quench/wash system permits the omission of reaction gas cooler and reduces cycle gas pressure drop, saving power. The improved quench purge column design reduces contamination of EO reabsorbate feed to glycol reaction and improves MEG quality. Other glycol reaction improvements resulting from the present invention include: Raising the economically optimum range of water/EO ratios in the glycol reactor feed (EO reabsorbate) by increasing the stripper bypass, making the use of very high water ratios (up to 40:1) justifiable and results in reduced DEG/TEG production with higher yields of MEG; injecting extracted low pressure process steam from the glycol plant directly into the bottom of the EO stripper provides up to 100% of the required stripping steam; Sending the aqueous bleed stream from the quench/wash section to a separate purge stripper, designed for low liquid holdup time to minimize EO hydration to MEG, in which absorbed EO is completely stripped out for recovery as feed to the fiber-grade MEG reactor; Cooling the purge stripper overhead vapors to condense a substantial part (preferably at least 60%) of the water vapor and returning the condensate, contaminated with entrained salts and condensed formaldehyde, back to the top of the purge stripper. The uncondensed EO-rich vapor from the partial condenser is then pure enough to be combined with the main EO stripper overhead vapor for recovery of its EO content in the reabsorber or residual absorber.

Elimination of need for prior glycol treatment systems saves capital and operating cost. The present incorporation of quench/wash and quench purge stripper system purges most of formaldehyde made in EO reaction to waste and radically reduces a formaldehyde buildup in glycol reaction system which permits use of ultra high selectivity EO catalysts. As water/EO ratio in glycol reactor feed (EO reabsorbate) is increased, the stripper bypass can be increased, making the use of very high water ratios (up to 35:1) economically justifiable and resulting in higher yields of MEG.

A high "purge" rate of stripper cycle water to glycol plant results in very low equilibrium glycol concentration in cycle water with reduced foaming and improved column efficiency and capacity and permits direct injection of very low pressure process steam extracted from glycol plant into EO stripper to provide up to 100% of the required stripping steam.

The invention claimed is:

1. In the process or recovering ethylene oxide from a vaporous reaction stream containing ethylene oxide, $CO_2$, formaldehyde, acetylaldehyde, and organic acidic compounds comprising:
   absorption of ethylene oxide and a portion of said $CO_2$, formaldehyde, acetylaldehyde, and organic acidic compounds in water to form an absorption stream;
   contacting said absorption stream with steam to strip ethylene oxide, $CO_2$, formaldehyde, acetylaldehyde, and organic acidic compounds from said absorption stream to form a stripping stream
   condensing water, formaldehyde, a portion of the ethylene oxide, acetaldehyde and organic acidic compounds; and
   recovering a vaporous ethylene oxide product stream; and
   contacting the vaporous ethylene oxide product stream in an EO absorber where it is countercurrently washed with recirculated EO-free process water to absorb the ethylene oxide to produce EO containing absorbate:

wherein the improvement comprises sending a portion comprising 10-90% of the dilute EO containing absorbate from the EO absorber directly to a EO reabsorber/residual absorber where said dilute EO containing absorbate absorbs additional EO from an EO stripper overhead vapor to produce high-purity EO/water solution of the desired EO concentration for use as feed to a glycol production reaction.

* * * * *